United States Patent
Feugnet et al.

(10) Patent No.: US 11,203,718 B2
(45) Date of Patent: *Dec. 21, 2021

(54) PROCESS FOR PRODUCING BTX BY CATALYTIC PYROLYSIS FROM BIOMASS WITH INJECTION OF OXYGENATED COMPOUNDS

(71) Applicant: IFP Energies Nouvelles, Rueil-Malmaison (FR)

(72) Inventors: Frederic Feugnet, Lyons (FR); Nicolas Lopes Ferreira, Croisilles (FR); Slavik Kasztelan, Lyons (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 342 days.

This patent is subject to a terminal disclaimer.

(21) Appl. No.: 16/305,198

(22) PCT Filed: May 3, 2017

(86) PCT No.: PCT/EP2017/060549
§ 371 (c)(1),
(2) Date: Nov. 28, 2018

(87) PCT Pub. No.: WO2017/207202
PCT Pub. Date: Dec. 7, 2017

(65) Prior Publication Data
US 2020/0255743 A1  Aug. 13, 2020

(30) Foreign Application Priority Data
May 31, 2016  (FR) ...................................... 1654892

(51) Int. Cl.
| | | |
|---|---|---|
| *C10B 49/22* | (2006.01) | |
| *C10G 3/00* | (2006.01) | |
| *C10B 53/02* | (2006.01) | |
| *C10B 57/06* | (2006.01) | |
| *C12P 7/04* | (2006.01) | |
| *C12P 7/06* | (2006.01) | |
| *C12P 7/16* | (2006.01) | |

(52) U.S. Cl.
CPC ................ *C10G 3/49* (2013.01); *C10B 49/22* (2013.01); *C10B 53/02* (2013.01); *C10B 57/06* (2013.01); *C12P 7/04* (2013.01); *C12P 7/06* (2013.01); *C12P 7/16* (2013.01); *C10G 2300/1011* (2013.01); *C10G 2400/30* (2013.01)

(58) Field of Classification Search
None
See application file for complete search history.

(56) References Cited

U.S. PATENT DOCUMENTS

| | | |
|---|---|---|
| 9,249,080 B2 | 2/2016 | Mazanec et al. |
| 9,845,279 B2 | 12/2017 | Mazanec et al. |
| 2014/0107306 A1 | 4/2014 | Mazanec et al. |
| 2014/0134686 A1 | 5/2014 | Schultz et al. |
| 2015/0218078 A1 | 8/2015 | Mazanec et al. |

OTHER PUBLICATIONS

International Search Report dated Jun. 20, 2017 issued in corresponding PCT/EP2017/060549 application (3 pages).
H. Zhang et al., "Catalytic Fast Pyrolysis of Wood and Alcohol Mixtures in a Fluidized Bed Reactor", Green Chemistry, vol. 14, No. 1 (Jan. 2012) pp. 98-110.
Y-T Cheng et al., "Production of Renewable Aromatic Compounds by Catalytic Fast Pyrolysis of Lignocellulosic Biomass with Bifunctional Ga/ZSM-5 Catalysts", Angewandte Chemie International Edition, vol. 51, No. 6 (2012) pp. 1387-1390.
T.R. Carlson et al., "Aromatic Production from Catalytic Fast Pyrolysis of Biomass-Derived Feedstocks", Topics in Catalysis, vol. 52, No. 3 (2009) pp. 241-252.

*Primary Examiner* — Heidi Reese
(74) *Attorney, Agent, or Firm* — Millen, White, Zelano and Branigan, P.C.

(57) ABSTRACT

A process is described for producing a BTX cut from biomass comprising at least one step of catalytic pyrolysis of said biomass in a fluidized-bed reactor in which a stream comprising at least one oxygenated compound selected from alcohols having 2 to 12 carbon atoms, alcohol acids having 2 to 12 carbon atoms, diols having 2 to 12 carbon atoms, carboxylic acids having 2 to 12 carbon atoms, ethers having 2 to 12 carbon atoms, aldehydes having 2 to 12 carbon atoms, esters having 2 to 12 carbon atoms and glycerol, alone or mixed, is fed into the catalytic pyrolysis reactor.

13 Claims, 1 Drawing Sheet

PROCESS FOR PRODUCING BTX BY CATALYTIC PYROLYSIS FROM BIOMASS WITH INJECTION OF OXYGENATED COMPOUNDS

FIELD OF TECHNOLOGY

Chemical intermediates are normally produced from fossil resources such as petroleum, natural gas or coal in multistep processes. In order to replace or supplement the production of chemical intermediates from fossil resources, it is necessary to develop methods for treating non-fossil feedstocks, namely biomass. The present invention relates to a process for producing chemical intermediates and/or bases for motor fuel and in particular BTX starting from biomass.

The present invention relates to a process for producing a BTX cut from biomass and more particularly a process for producing a BTX cut by catalytic pyrolysis of biomass, preferably lignocellulosic, catalytic pyrolysis being carried out in the presence of a stream of specific oxygenated compounds.

PRIOR ART

U.S. Pat. No. 8,277,643 describes a process for producing aromatics, biofuel and olefins by catalytic pyrolysis of biomass in the presence of a zeolite catalyst such as ZSM-5. The process is carried out at a temperature at least above 300° C., at a pressure between 1 and 4 atm, and at an LHSV between 0.01 and 10 h-1. The process is also characterized by a residence time of the biomass in the reactor of between 2 seconds and 5 minutes.

Patent application WO2009/111026 describes more precisely the type of catalyst that can be used in the catalytic pyrolysis step and in particular zeolite catalysts that can be doped with iron, gallium or zinc.

Patent application WO2011/031320 describes a process for producing aromatics, biofuel and olefins by catalytic pyrolysis of biomass in the presence of a zeolite catalyst, in which the products obtained by pyrolysis are separated so as to obtain a fraction comprising olefins that is then recycled to the pyrolysis reactor.

Thus, the applicant discovered that by employing a process for producing a BTX cut by catalytic pyrolysis of lignocellulosic biomass in the presence of a stream of specific oxygenated compounds it was possible to obtain an improved yield of BTX relative to the processes of the prior art.

SUMMARY AND BENEFITS OF THE INVENTION

The invention relates to a process for producing a BTX cut from biomass comprising at least one step of catalytic pyrolysis of said biomass in a fluidized-bed reactor in which a stream comprising at least one oxygenated compound selected from alcohols having 2 to 12 carbon atoms, alcohol acids having 2 to 12 carbon atoms, diols having 2 to 12 carbon atoms, carboxylic acids having 2 to 12 carbon atoms, ethers having 2 to 12 carbon atoms, aldehydes having 2 to 12 carbon atoms, esters having 2 to 12 carbon atoms and glycerol, alone or mixed, is fed into the catalytic pyrolysis reactor.

Hereinafter, BTX cut means a fraction comprising a mixture of Benzene, Toluene and Xylenes (ortho, meta, para).

An advantage of the present invention is therefore that it supplies a process for producing BTX allowing an improved yield of BTX to be obtained relative to the prior art, by employing a step of catalytic pyrolysis of biomass operating in the presence of a stream of quite specific oxygenated compounds.

In the preferred embodiment of the invention, where the stream of oxygenated compounds is produced in a step of fermentation of a residual effluent from catalytic pyrolysis comprising carbon monoxide and carbon dioxide, an advantage of the present invention is that it supplies an integrated process for producing BTX in high yield by catalytic pyrolysis of biomass, followed by a fermentation step of conversion of a proportion of the residual gaseous effluent from pyrolysis comprising CO and $CO_2$, said process also allowing production of a stream of oxygenated compounds and in particular of alcohol and preferably of ethanol.

Another advantage of this embodiment of the present invention is therefore that it supplies a process allowing the simultaneous production of a BTX cut and of a stream of oxygenated compounds and preferably of alcohols such as ethanol, at least a proportion of said stream of oxygenated compounds being used for increasing the production of the BTX cut, thus increasing the flexibility of the process according to the invention.

Another advantage of this embodiment of the present invention is upgrading of the purge of said recycle gas fraction comprising CO and $CO_2$ produced by catalytic pyrolysis in a fermentation step for producing at least one oxygenated compound as claimed and preferably ethanol, therefore allowing a marked improvement in profitability of the process according to the invention.

Another advantage of this embodiment of the present invention is therefore optimization of the upgrading of the carbon obtained from biomass, in particular into chemical intermediates such as BTX, but also into bases for biofuel.

Another advantage of this embodiment of the present invention is that it supplies an optimized process for producing a BTX cut, in that the gaseous effluent comprising CO and $CO_2$ produced by catalytic pyrolysis and used as feed for the fermentation step is withdrawn from the step of catalytic pyrolysis at a temperature and a pressure compatible with its direct use in a fermentation step, without an intermediate compression step. The gaseous effluent comprising CO and $CO_2$ produced by catalytic pyrolysis also has a composition compatible with its use in a fermentation step.

DETAILED DESCRIPTION OF THE INVENTION

According to the invention, the process is a process for producing a BTX cut from biomass comprising at least one step of catalytic pyrolysis of said biomass in a fluidized-bed reactor in which a stream comprising at least one oxygenated compound selected from alcohols having 2 to 12 carbon atoms, alcohol acids having 2 to 12 carbon atoms, diols having 2 to 12 carbon atoms, carboxylic acids having 2 to 12 carbon atoms, ethers having 2 to 12 carbon atoms, aldehydes having 2 to 12 carbon atoms, esters having 2 to 12 carbon atoms and glycerol, alone or mixed, is fed into the catalytic pyrolysis reactor.

Examples of fluidized-bed reactors may be found in Howard, R. J. (1989). "Principles of fluidized-bed technology and applications." New York, Adam Higler of N.Y.; Tavoulareas, S. (1991) fluidized-bed Combustion Technology. Annual Reviews Inc 16, 25-27, and Trambouze, P., and Euzen, J. (2004). "Chemical reactors: From design to operation." (R. Bonormo, Trans.). Paris: Editions Technip.

The fluidized-bed reactor used in the process according to the invention preferably operates in turbulent conditions, i.e. in a range of surface gas velocity between 0.5 and 0.8 m/s. Surface gas velocity means the volume flow rate of gas referred to the surface area of the reactor.

This turbulent-bed application is favoured relative to the so-called "riser" technology usually employed for FCC, in that there are high yields of coke and of incompletely converted biomass usually called "char" in FCC technology, and consequently there is a high concentration of coke on the catalyst. In the proposed application, the heat balance of the catalytic pyrolysis step is decoupled by regulating the residence time of the catalyst in the reactor via the rate of withdrawal of the latter to the regenerator, thus making it possible to limit the percentage of coke on the catalyst and therefore limit the temperature of the regenerator within an operable range.

According to the invention, the feedstock used in the present invention is biomass.

Preferably, the feedstock is lignocellulosic biomass or one or more constituents of lignocellulosic biomass selected from the group comprising cellulose, hemicellulose and/or lignin.

Lignocellulosic biomass may consist of wood, agricultural waste or vegetable waste. Other non-limiting examples of lignocellulosic biomass material are farm residues (straw, maize stover, etc.), forestry residues (products from first thinning), forestry products, dedicated crops (short rotation coppice), food industry residues, organic household waste, waste from woodworking plant, wood used in construction, paper, whether or not recycled.

Lignocellulosic biomass may also come from by-products of the papermaking industry such as Kraft lignin, or black liquor from manufacture of pulp for paper.

The lignocellulosic biomass may advantageously undergo at least one step of pretreatment before it is fed into the process according to the invention. Preferably, the biomass is ground and dried, until the desired granulometry is obtained. A feed having a particle diameter between 0.3 and 0.5 mm may advantageously be obtained. Typically, the particle size of the lignocellulosic biomass for pyrolysis is a sufficient particle size to pass through a 1-mm sieve up to a sufficient particle size to pass through a 30-mm sieve.

Preferably, the biomass for pyrolysis is advantageously fed into a compartment for pneumatic entrainment or transport so as to be entrained into the fluidized-bed by an entraining fluid. Preferably, the entraining fluid used is gaseous nitrogen. However, it is also envisaged that other non-oxidizing entraining fluids may be used. Preferably, the pyrolysis gas produced during the process may be recycled and used as entraining fluid. Said pyrolysis gas advantageously mainly consists of light olefins from C2 to C4 produced in step a). In this way, the cost of carrying out pyrolysis can be reduced considerably. The biomass may be supplied in a feed hopper or some other device that makes it possible to feed the biomass into the entrainment compartment in a suitable amount. In this way, a constant amount of biomass is delivered into the entrainment compartment.

The entraining fluid advantageously transports the biomass from the entrainment compartment into the fluidized bed through a feed tube. Typically, the feed tube is cooled to maintain the temperature of the biomass at a required level before it enters the fluidized bed. The feed tube may be cooled by jacketing the tube, typically with an air-cooled or liquid-cooled jacket. However, it is also envisaged that the feed tube is not cooled.

According to the invention, the catalytic pyrolysis step operates in the presence of a catalyst. Preferably, said step operates in the presence of a zeolite catalyst comprising and preferably consisting of at least one zeolite selected from ZSM-5, ferrierite, zeolite Beta, zeolite Y, mordenite, ZSM-23, ZSM-57, EU-1, ZSM-11 and preferably the catalyst is a catalyst comprising only ZSM-5. The zeolite used in the catalyst employed in the catalytic pyrolysis step may advantageously be doped preferably with a metal selected from iron, gallium, zinc and lanthanum.

The temperature employed in the catalytic pyrolysis step may be adjusted in relation to the catalyst used and the desired reaction products. In certain embodiments, the catalytic pyrolysis step is carried out at a temperature between 400 and 1000° C., preferably between 400 and 650° C., preferably between 450 and 600° C. and preferably between 450 and 590° C. In particular, it is the catalyst obtained from the regeneration step that makes it possible to provide these temperature ranges of the reactor.

The pyrolysis step is also advantageously carried out at an absolute pressure between 0.1 and 0.5 MPa and at an LHSV between 0.01 and 10 h-1, preferably between 0.01 and 5 h-1, preferably between 0.1 and 3 h-1 and very preferably between 0.1 and 3 h-1.

In these conditions, the biomass will firstly undergo rapid pyrolysis in the reactor on coming into contact with the hot catalyst obtained from the regenerator, which performs the role of heat carrier in this step. The gases resulting from this pyrolysis will then react on the catalyst, which this time performs its role of catalyst for catalysing the reactions that produce the required chemical intermediates.

The products obtained at the end of the catalytic pyrolysis step are advantageously recovered in the form of a gaseous effluent comprising at least a proportion of the BTX cut. Said gaseous effluent comprising the products obtained at the end of the catalytic pyrolysis step is then advantageously sent to a fractionation section, so as to separate at least the following cuts:
 a non-condensable gaseous effluent, comprising at least carbon monoxide (CO) and carbon dioxide ($CO_2$),
 a liquid cut called BTX,
 a liquid cut predominantly comprising compounds having a number of carbon atoms greater than 9, i.e. at least 50 wt % of C9+ compounds, and
 water.

Said non-condensable gaseous effluent, comprising at least carbon monoxide (CO) and carbon dioxide ($CO_2$), also advantageously comprises light olefins comprising from 1 to 4 carbon atoms.

The coked catalyst and the unconverted biomass, usually called "char", are advantageously withdrawn from the reactor and preferably sent to a stripper so as to remove the hydrocarbons potentially adsorbed, and thus prevent their combustion in the regenerator, by contacting with a gas selected from steam, an inert gas such as nitrogen for example and at least a proportion of the non-condensable gaseous cut rich in CO and $CO_2$ resulting from fractionation of the gaseous effluent from the catalytic pyrolysis step.

Said coked catalyst and the char, optionally stripped, are advantageously sent to a regenerator, where coke and char are burned by adding air or oxygen.

The catalyst thus regenerated is advantageously recycled to the reactor of the catalytic pyrolysis step in order to undergo another cycle.

The catalytic pyrolysis step of the process according to the invention allows production of at least 10 wt % and preferably at least 15 wt % of aromatics relative to the total weight of the reaction products obtained, with a selectivity of at least 65% and preferably of at least 70% of BTX.

The process according to the invention comprising at least one step of catalytic pyrolysis of a biomass feed therefore produces at least one BTX cut and a gas fraction comprising at least carbon monoxide and carbon dioxide.

The process also makes it possible to obtain, in addition to the BTX cut, a heavier liquid fraction, predominantly aromatic, called "C9+ cut", which may advantageously be upgraded in a process external to the process according to the invention.

Preferably, at least a proportion of said gaseous effluent comprising carbon monoxide (CO) and carbon dioxide ($CO_2$) is recycled, preferably via a compressor, to the reactor of the catalytic pyrolysis step. This gaseous stream then serves as fluid for entraining the feed into said reactor.

In this case, purge of said gaseous recycle effluent is inevitable and is preferably carried out, either upstream, or downstream of said compressor.

According to the invention, the step of catalytic pyrolysis of the biomass operates in the presence of a stream comprising at least one oxygenated compound selected from alcohols having 2 to 12 carbon atoms, alcohol acids having 2 to 12 carbon atoms, diols having 2 to 12 carbon atoms, carboxylic acids having 2 to 12 carbon atoms, ethers having 2 to 12 carbon atoms, aldehydes having 2 to 12 carbon atoms, esters having 2 to 12 carbon atoms and glycerol, alone or mixed.

Preferably, said step of catalytic pyrolysis of biomass operates in the presence of a stream comprising at least one oxygenated compound selected from alcohols having 2 to 6 carbon atoms and preferably alcohols having 2 to 4 carbon atoms, alcohol acids having 2 to 6 carbon atoms, diols having 2 to 6 carbon atoms and preferably diols having 2 to 4 carbon atoms, carboxylic acids having 2 to 6 carbon atoms and preferably carboxylic acids having 2 to 4 carbon atoms, ethers having 2 to 6 carbon atoms, aldehydes having 2 to 6 carbon atoms and esters having 2 to 6 carbon atoms and glycerol.

Very preferably, said step of catalytic pyrolysis of biomass operates in the presence of a stream comprising at least one oxygenated compound selected from alcohols having 2 to 6 carbon atoms, and preferably alcohols having 2 to 4 carbon atoms, diols having 2 to 6 carbon atoms and preferably diols having 2 to 4 carbon atoms, alcohol acids having 2 to 4 carbon atoms and carboxylic acids having 2 to 6 carbon atoms and preferably carboxylic acids having 2 to 4 carbon atoms, alone or mixed.

Preferably, the alcohols have 2 to 12 carbon atoms in said stream of oxygenated compounds and are selected from ethanol, n-propanol and isopropanol, butanol, isobutanol, 2,3-butanediol, isononanol, 2-ethylhexanol and hexanol, alone or mixed, and preferably said alcohols are selected from ethanol, n-propanol and isopropanol, butanol, isobutanol, 2,3-butanediol and hexanol, alone or mixed.

Preferably, the alcohol acids having 2 to 12 carbon atoms and preferably 2 to 6 carbon atoms are selected from lactic acid ($C_3H_6O_3$), tartaric acid ($C_4H_6O_6$), citric acid ($C_6H_8O_7$), glycolic acid ($C_2H_4O_3$), the carboxylic acids having 2 to 12 and preferably 2 to 6 carbon atoms are selected from acetic acid, butyric acid, pyruvic acid and hexanoic acid, alone or mixed, and the diols having 2 to 12 and preferably 2 to 6 carbon atoms are selected from ethylene glycol, diethylene glycol, triethylene glycol, propylene glycol (propane-1,2-diol), trimethylene glycol (propane-1,3-diol), butylene glycol (butane-1,3-diol), n-butylene glycol (butane-1,4-diol) and 2,3-butylene glycol (butane-2,3-diol), alone or mixed.

Preferably, the ethers having 2 to 12 carbon atoms and preferably 2 to 6 carbon atoms are selected from dimethyl ether, methyl ethyl ether, diethyl ether, methyl propyl ether, methyl tert-butyl ether, ethyl tert-butyl ether, tetrahydrofuran, alone or mixed.

Preferably, the aldehydes having 2 to 12 carbon atoms and preferably 2 to 6 carbon atoms are selected from ethanal, propanal, butanal, pentanal, 3-methylbutanal, hexanal, furfural and glyoxal, alone or mixed.

Preferably, the esters having 2 to 12 carbon atoms and preferably 2 to 6 carbon atoms are selected from methyl formate, methyl acetate, methyl propionate, methyl butanoate, methyl pentanoate, ethyl acetate, propyl acetate, isopropyl acetate, butyl acetate, isobutyl acetate, and butyl butyrate, alone or mixed.

Preferably, said step of catalytic pyrolysis of biomass operates in the presence of a stream comprising at least one oxygenated compound selected from ethanol, n-propanol, isopropanol, butanol, isobutanol, hexanol, acetic acid, butyric acid, hexanoic acid, lactic acid and 2,3-butylene glycol (butane-2,3-diol), alone or mixed.

Said stream comprising at least one oxygenated compound fed into the catalytic pyrolysis reactor advantageously comes from any process external to the process according to the invention allowing production of streams of oxygenated compounds such as, for example for the alcohols, hydration of olefins, hydrogenation of aldehydes, hydrogenation of acids and dicarboxylic acids or hydrogenation of sugars, for the aldehydes; oxidation of alcohols, carbonylation of olefins, for the ethers; etherification, dehydration of alcohols, for the esters; transesterification, esterification of carboxylic acids, and carbonylation.

In a much preferred embodiment, said stream comprising at least one oxygenated compound is produced in a step of fermentation of a residual effluent from the catalytic pyrolysis step of the process according to the invention, said residual effluent comprising carbon monoxide and carbon dioxide.

Hereinafter, the terms "fermentation", "fermentation step", or "fermentation reaction" relate to conversion of the gases $H_2$, CO and/or $CO_2$ and include both the growth phase of the fermenting microorganism and the phase of production of the molecules of interest, such as alcohols, acids, alcohol acids and/or carboxylic acids by this microorganism.

Very preferably, said stream comprising at least one oxygenated compound is produced in a step of fermentation of a proportion of the gaseous effluent from pyrolysis comprising CO and $CO_2$, and even more preferably, said stream is produced in a step of fermentation of the purge of the gaseous recycle effluent comprising CO and $CO_2$ produced by catalytic pyrolysis in the process according to the invention.

In this much preferred embodiment, said process according to the invention advantageously comprises at least the following steps:
  a) catalytic pyrolysis of biomass in a fluidized-bed reactor producing at least one BTX fraction and a gaseous effluent comprising at least carbon monoxide and carbon dioxide;
  b) recycling at least a proportion of said gaseous effluent comprising at least carbon monoxide and carbon dioxide to the reactor in said step a),
  c) purge of said one gaseous recycle effluent according to step b), d) sending at least a proportion of said purge in step c) to a fermentation step producing a liquid fermentation stream comprising at least one stream comprising at least one oxygenated compound selected from alcohols having 2 to 6 carbon atoms, diols having 2 to 4 carbon atoms, alcohol acids having 2 to 4 carbon atoms, carboxylic acids having 2 to 6 carbon atoms, aldehydes having 2 to 12 carbon atoms and esters having 2 to 12 carbon atoms, alone or mixed, e) recycling at least a proportion of said liquid fermentation stream comprising said stream of oxygenated compounds to the reactor in said step a) of catalytic pyrolysis.

Another advantage of the preferred embodiment of the present invention is that it supplies a process allowing production both of a BTX cut and of a stream of oxygenated compounds and preferably of a stream of compounds comprising ethanol, said process having a high yield of BTX by employing recycling, in the catalytic pyrolysis step, of a proportion of the stream of oxygenated compounds and in particular of the ethanol produced by the fermentation step.

Preferably, at least a proportion of said purge in step c) comprising carbon monoxide (CO) and carbon dioxide ($CO_2$) is sent to a fermentation step d) producing at least one stream comprising at least one oxygenated compound selected from alcohols having 2 to 6 carbon atoms, diols having 2 to 4 carbon atoms, alcohol acids having 2 to 4 carbon atoms, alcohol acids having 2 to 4 carbon atoms and carboxylic acids having 2 to 6 carbon atoms, alone or mixed, and very preferably, a stream comprising at least one oxygenated compound selected from ethanol, n-propanol, isopropanol, butanol, isobutanol, hexanol, acetic acid, butyric acid, hexanoic acid, lactic acid and 2,3-butylene glycol (butane-2,3-diol), alone or mixed.

In this preferred embodiment, the proportion by weight of said stream comprising at least one oxygenated compound produced by a fermentation step and recycled to the catalytic pyrolysis step represents advantageously 0.01 to 20 wt % and preferably 0.05 to 10 wt % of the weight of biomass fed into the process according to the invention.

Said purge of said recycle gas fraction generally comprises a carbon monoxide (CO) content advantageously between 30 and 60 wt % and a carbon dioxide ($CO_2$) content advantageously between 20 and 40 wt %.

Moreover, said purge also generally comprises hydrogen, C1-C4 light gases, olefins and may also contain a small content of aromatic impurities such as benzene and toluene for example.

The content of aromatic impurities may advantageously be decreased by adjusting the operating conditions of the catalytic pyrolysis step as well as the level of recycle returned to the reactor.

The gaseous effluent comprising CO and $CO_2$ produced by catalytic pyrolysis has a composition compatible with its use in a fermentation step.

Moreover, the portion of said purge in step c) comprising carbon monoxide (CO) and carbon dioxide ($CO_2$) used as feed for the fermentation step d) is withdrawn from step a) of catalytic pyrolysis at a temperature and a pressure compatible with its direct use in a fermentation step. The process according to the invention may require compressing or decompressing said purge to allow better operation of the fermentation step. In a preferred embodiment, the process according to the invention comprises neither a step of compression nor of heating of said purge in step c) comprising carbon monoxide (CO) and carbon dioxide ($CO_2$) to give operating conditions compatible with a fermentation step.

The portion of said purge in step c) comprising carbon monoxide (CO) and carbon dioxide ($CO_2$) used as feed for the fermentation step d) is generally withdrawn at a temperature between 20 and 60° C. and at a pressure between 0.1 and 0.5 MPa.

The fermentation step d) is advantageously carried out in the presence of at least one microorganism, also called acetogenic strain.

In fact, the ability of certain microorganisms to grow on gaseous substrates like carbon monoxide (CO), carbon dioxide ($CO_2$) and/or hydrogen ($H_2$) as the sole carbon source was discovered back in 1903. A large number of anaerobic organisms, more particularly the organisms called "acetogens", possess this ability to metabolize CO and/or the $CO_2/H_2$ pair to produce various final molecules of interest such as acetate, butyrate, ethanol and/or n-butanol.

The microorganisms capable of performing this fermentation process are mainly from the genus *Clostridium*, but other microorganisms, for example such as those from the genera *Acetobacteria, Butyribacterium, Desulfobacterium, Moorella, Oxobacter* or *Eubacteria* may also be used for carrying out this fermentation process.

The microorganisms are therefore selected so as to lead to production of the desired products in the fermentation step. The fermentation products may include, for example, alcohols and acids.

For example, various patents describe strains capable of producing the aforementioned products of interest, starting from synthesis gas. Among the acetogenic strains of the genus *Clostridium*, we may mention U.S. Pat. No. 5,173,429 describing a strain of *Clostridium ljungdahlii* (ATCC 49587) that produces ethanol and acetate. Other strains of the same species are described in documents WO 2000/68407, EP117309, U.S. Pat. Nos. 5,173,429, 5,593,886 and 6,368,819, WO1998/00558 and WO2002/08438. Certain strains of *Clostridium* such as the strains of *Clostridium autoethanogenum* (DSM 10061 and DSM 19630) described in documents WO2007/117157 and WO2009/151342, *Clostridium ragsdalei* (P11, ATCC BAA-622) described in U.S. Pat. No. 7,704,723 or *Clostridium carboxidivorans* (ATCC PTA-7827) described in patent application US2007/0276447, are also capable of producing molecules of interest by fermentation starting from gases ($H_2$, CO and/or $CO_2$).

Said microorganism or microorganisms or acetogenic strains used in the fermentation step of the process according to the invention are preferably selected from the following microorganisms: *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneus, Caldanaerobacter pacificus subterraneus, Hydrogenoformans carboxydothermus, Clostridium aceticum, Clostridium acetobutylicum, Clostridium acetobutylicum* P262 (DSM 19630 from DSMZ Germany), *Clostridium autoethanogenum* (DSM 19630 from DSMZ Germany), *Clostridium autoethanogenum* (DSM 10061 from DSMZ Germany), *Clostridium autoethanogenum* (DSM 23693 from DSMZ Germany), *Clostridium autoethanogenum* (DSM 24138 from DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ERI2 ljungdahlii* (ATCC 55380), *Clostridium ljungdahlii* C-01 (ATCC 55988), *Clostridium ljungdahlii* O-52 (ATCC 55889),

*Clostridium magnum, Clostridium pasteurianum* (DSM 525 from DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Sulfurreducens geobacter, Methanosarcina acetivorans, Methanosarcina barken, Morrella thermoacetica, Morrella thermoautotrophica, Oxobacter pfennigii, Peptostreptococcus productus, Ruminococcus productus, Thermoanaerobacter kivui*, and mixtures thereof.

Moreover, it has to be understood that other microorganisms capable of assimilating $H_2$, CO (otherwise called carboxidotrophs) and/or $CO_2$ as source of carbon may also be used in step d) of the present invention. All of the aforementioned microorganisms are called anaerobic, i.e. incapable of growing in the presence of oxygen. However, aerobic microorganisms may also be used, such as microorganisms belonging to the species *Escherichia coli*. For example, in one work it has been demonstrated that it is possible to produce a strain that is genetically modified for expressing the genes coding for the enzymes responsible for assimilation of CO (genes of the Wood-Ljungdahl metabolic pathway) in order to produce molecules of interest, such as isopropanol, starting from an important metabolic intermediate: acetyl CoA (Trawick, J. D.; Burk, M. J.; Burgard, A. P. Microorganisms and Methods for Conversion of Syngas and Other Carbon Sources to Useful Products. Patent WO2010/071697). Burk, M.; Schilling, C. H.; Burgard, A.; Trawick, J. D. Methods and Organisms for Utilizing Synthesis Gas or Other Gaseous Carbon Sources and Methanol. Patent WO2009/094485). Other genetically modified microorganisms have been described for producing isopropanol, for example the microorganism *C. ljungdahlii* (US2012/0252083; Lanzatech).

In preferred embodiments, the microorganisms are selected from *Clostridium autoethanogenum, Clostridium ljungdahlii, Clostridium aceticum, Morella thermoacetica, Acetobacterium woodii* and *Alkalibaculum bacchi* for producing ethanol and/or acetate, *Clostridium autoethanogenum, Clostridium ljungdahlii* and *C. ragdalei* for producing 2,3-butanediol and *Clostridium carboxidivorans, Clostridium drakei, Clostridium scatologenes* or *Butyribacterium methylotrophicum* for producing butyrate and butanol.

Cultures comprising a mixture of two or more microorganisms may also be used.

The fermentation step d) may advantageously be carried out aerobically or anaerobically and preferably anaerobically.

The fermentation step d) is advantageously carried out in one or more reactors or "bioreactors".

The term "bioreactor" comprises a fermentation device consisting of one or more tanks or tubular reactors, comprising the devices of the type CSTR or Continuous Stirred Reactor Reservoir using the English-language terminology, ICR or Immobilized Cell Reactor using the English-language terminology, TBR or Trickle Bed Reactor, fermenters of the Gas Lift type, bubble columns, or membrane reactor such as the HFMBR system or Hollow Fibre Membrane Bio-Reactor using the English-language terminology, a static mixer, or any other suitable device for gas-liquid contact.

The portion of said purge in step c) comprising carbon monoxide (CO) and carbon dioxide ($CO_2$) used as feed for the fermentation step d) is fed into the fermentation reactor or reactors in the form of a gaseous substrate. Each fermentation reactor contains a culture medium.

Preferably, the required concentration of gaseous substrate from the purge (CO, $CO_2$, $H_2$) in the culture medium of said fermentation reactor or reactors is at least 2.5 mmol/L of CO and/or $CO_2$.

The portion of the purge in step c) used as feed for the fermentation step d) is fed into the fermentation reactor or reactors in the form of a gaseous substrate advantageously containing a high content of CO, preferably a content between 2 and 100 wt % of CO, preferably a content between 20 and 100 wt % of CO, very preferably between 30 and 95 wt % of CO, more preferably between 35 and 80 wt % of CO, and even more preferably between 40 and 60 wt % of CO.

Preferably, the portion of said purge in step c) used as feed for the fermentation step d) in the form of gaseous substrate advantageously has a weight ratio $H_2$/CO between 0 and 1.2 and preferably between 0.5 and 1.2 and very preferably between 0.5 and 1.1 or $H_2/CO_2$ between 0 and 1.7 and preferably between 1 and 1.7 and very preferably between 1.2 and 1.6.

According to a preferred embodiment, fermentation step d) comprises a chain of propagation of an acetogenic strain in order to supply a sufficient quantity of cells for inoculating a main reactor, said chain of propagation comprising: i) inoculation of the acetogenic strain in a first propagation reactor supplying a minimum density of viable cells for a second propagation reactor having a larger volume, and ii) growth of said acetogenic strain in the second reactor to supply a density of cells suitable for inoculating a third propagation reactor, the largest in terms of volume. If necessary, the chain of propagation may comprise a larger number of propagation reactors.

The fermentation step also comprises a production step in which the fermentation process is optimum, i.e. in which the molecules of interest are produced in great quantity. The stream comprising at least one oxygenated compound as claimed is therefore produced in said production step.

Preferably, the propagation step may be carried out in one or more reactors for propagation of the microorganism, all of these reactors being connected to allow transfer of the microbial culture.

One or more "production" reactors in which the fermentation process takes place are also employed.

The microorganisms or acetogenic strains are generally cultured until an optimum cell density is obtained for inoculating the production reactors. This level of inoculum may vary from 0.5 to 75%, which makes it possible to have production reactors that are larger than the propagation reactors. Thus, the propagation reactor can be used for seeding several other larger production reactors.

In the case when the fermentation step comprises a propagation step and a production step, the portion of said purge in step c) comprising carbon monoxide (CO) and carbon dioxide ($CO_2$) may advantageously be introduced in the fermentation step at the level of the reactors of the production step.

At least one additional carbon-containing substrate may advantageously be used in combination with the gaseous substrates obtained from the purge, for growing the microorganisms in the propagation step. Said carbon-containing substrate may advantageously be selected from the n-monosaccharides such as glucose, fructose or xylose, the polysaccharides such as starch, sucrose, lactose or cellulose, the metabolic intermediates such as pyruvate or any other carbon-containing substrate known by a person skilled in the art as being assimilable by the microorganisms used in the process. Said carbon-containing substrate may also be a mixture of two or more of these carbon-containing substrates.

Control of the operating conditions is also necessary for optimizing the execution of the fermentation step. As an example, Lowe et al. (Microbiological Review, 1993 57:451-509), or Henstra et al. (Current Opinion in Biotechnology 2007, 18:200-206), summarize the optimum operating conditions in terms of temperatures and pH, for growing the microorganisms usable in the fermentation process. The pH is one of the most important factors for the fermentation activity of the microorganisms used in the process. Preferably, said fermentation step d) is carried out at a pH between 3 and 9, preferably between 4 and 8, and more preferably between 5 and 7.5.

Temperature is also an important parameter for improving fermentation as it has an influence both on microbial activity and on the solubility of the gases used as substrate. The choice of temperature depends on the microorganism used, certain strains being capable of growing in moderate temperature conditions (strains called mesophiles) and others in conditions of high temperatures (thermophilic microorganisms). Preferably, said fermentation step d) is carried out at a growing temperature between 20 and 80° C. Preferably, said fermentation step d) is carried out at a growing temperature between 20 and 40° C. for the mesophilic strains and preferably between 25 and 35 and between 40 and 80° C. for the thermophilic strains and preferably between 50 and 60° C.

The oxidation-reduction potential (redox potential) is also an important parameter to be controlled in the fermentation process. The redox potential is preferably below 450 mV (Ag/AgCl electrode) and preferably between 150 and 250 mV (Ag/AgCl electrode).

Moreover, said fermentation step is advantageously carried out at a pressure between 0.1 and 0.4 MPa.

The nutrient medium or culture medium of the fermentation step may advantageously contain at least one reducing agent so as to improve the performance of the fermentation process by controlling the redox potential of the fermentation step.

The nutrient medium may also comprise minerals, vitamins, metal co-factors or metals specific to the metalloenzymes involved in the routes for conversion of the gas into products of interest. Anaerobic nutrient media suitable for fermentation of ethanol using CO and/or $CO_2$ as the sole source(s) of carbon are known by a person skilled in the art. For example, suitable media are described in U.S. Pat. Nos. 5,173,429 and 5,593,886 and WO02/08438, WO2007/115157 and WO2008/115080 or the work of J. R. Phillips et al. (Bioresource Technology 190 (2015) 114-121).

The composition of the nutrient medium must allow efficient conversion of the gaseous substrate to a molecule of interest. This conversion is advantageously at least 5% and it may be up to 99%, preferably from 10 to 90%, and preferably 40 to 70%.

The nutrient medium may contain at least one or more sources of nitrogen, one or more sources of phosphorus and one or more sources of potassium. The nutrient medium may comprise one of these three compounds, or any combination of the three, and in an important aspect, the medium must comprise all three compounds. The source of nitrogen may be selected from ammonium chloride, ammonium phosphate, ammonium sulphate, ammonium nitrate, and mixtures thereof. The source of phosphorus may be selected from phosphoric acid, ammonium phosphate, potassium phosphate, and mixtures thereof. The source of potassium may be selected from potassium chloride, potassium phosphate, potassium nitrate, potassium sulphate, and mixtures thereof.

The nutrient medium may also comprise one or more metals such as iron, tungsten, nickel, cobalt, magnesium, sulphur and thiamine. The medium may comprise any one of these components, or any combination and in an important aspect it comprises all of these components. The source of iron may be selected from ferrous chloride, ferrous sulphate and mixtures thereof. The source of tungsten may be selected from sodium tungstate, calcium tungstate, potassium tungstate and mixtures thereof. The source of nickel may include a source of nickel selected from the group consisting of nickel chloride, nickel sulphate, nickel nitrate, and mixtures thereof. The source of cobalt may be selected from cobalt chloride, cobalt fluoride, cobalt bromide, cobalt iodide and mixtures thereof. The source of magnesium may be selected from magnesium chloride, magnesium sulphate, magnesium phosphate, and mixtures thereof. The source of sulphur may comprise cysteine, sodium sulphide, and mixtures thereof.

The fermentation step d) may also advantageously be carried out as described in patent applications WO2007/117157, WO2008/115080, U.S. Pat. Nos. 6,340,581, 6,136,577, 5,593,886, 5,807,722 and 5,821,111.

As mentioned above, the optimum operating conditions for carrying out this fermentation step depend partly on the microorganism or microorganisms used. The most important parameters to be controlled comprise the pressure, temperature, gas and liquid flow rate, pH of the medium, redox potential, stirring speed and the level of inoculum. It is also necessary to ensure that the contents of gaseous substrates in the liquid phase are not limiting. Examples of suitable operating conditions are described in patents WO02/08438, WO07/117157 and WO08/115080. The ratio of $H_2$ to the gaseous substrates CO and $CO_2$ may also be important for controlling the nature of the alcohols produced by the fermentation microorganisms. In patent application WO12/131627, it is for example described that depending on the level of hydrogen, it is possible to produce either ethanol alone, or ethanol and 2,3-butanediol if the $H_2$ percentage is below 20% (by volume). The typical composition of the purge gas fed to the production reactors would advantageously make it possible to produce 2,3-butanediol and ethanol by *Clostridium autoethanogenum*.

Preferably, fermentation should be carried out at a pressure above the ambient pressure. By employing an increased pressure it is possible to increase substantially the rate of transfer of gas to the liquid phase so that it is assimilated by the microorganism as a carbon source. This operation notably makes it possible to reduce the retention time (defined as the volume of liquid in the bioreactor divided by the flow rate of feed gas) in the bioreactor and therefore better productivity (defined as the number of grams of molecules of interest produced per litre and per day of production) of the fermentation process. Examples of productivity improvement are described in patent WO02/08438.

According to the preferred embodiment of the invention, said fermentation step d) produces a liquid fermentation stream comprising at least one stream comprising at least one oxygenated compound selected from alcohols having 2 to 6 carbon atoms, diols having 2 to 4 carbon atoms, alcohol acids having 2 to 4 carbon atoms, carboxylic acids having 2 to 6 carbon atoms, aldehydes having 2 to 12 carbon atoms and preferably 2 to 6 carbon atoms and esters having 2 to 12 carbon atoms and preferably 2 to 6 carbon atoms, alone or mixed, and very preferably, a stream comprising at least one oxygenated compound selected from ethanol, n-propanol, isopropanol, butanol, isobutanol, hexanol, acetic acid, butyric acid, hexanoic acid, lactic acid and 2,3-butylene glycol (butane-2,3-diol), alone or mixed.

Said liquid fermentation stream produced by the fermentation step d) also advantageously contains nutrient medium, molecules of interest (alcohols, alcohol acids, acids), i.e. a stream of oxygenated compounds as described above and bacterial cells.

Said liquid fermentation stream produced by the fermentation step d) may advantageously be separated so as to obtain said stream of oxygenated compounds. Said separation step is advantageously carried out by separation techniques known by a person skilled in the art. Said stream of oxygenated compounds produced by said fermentation step and separated from said liquid fermentation stream produced by the fermentation step d) may also advantageously be separated into different streams comprising said molecules of interest.

As an example, it is possible to recover the various alcohols produced, contained in said stream of oxygenated compounds, by methods such as distillation or fractional evaporation. Examples of techniques of this type comprise those described in WO2007/117157, WO2008/115080, U.S. Pat. Nos. 6,340,581, 6,136,577, 5,593,886, 5,807,722 and 5,821,111.

Distillation of alcohol from said stream of fermentation liquid obtained from said step d) may advantageously be carried out after passage through a beer column for obtaining a stream of concentrated alcohols and the optional recycling of the acids and other molecules reassimilable by the microorganism or microorganisms used in said fermentation step. The stream of alcohols may then be treated via various distillation columns allowing selective or non-selective separation of the various alcohols present. For this purpose, it is possible to use techniques of dehydration of alcohols, notably via molecular sieves, familiar to a person skilled in the art.

According to the invention, a stream comprising at least one oxygenated compound selected from alcohols having 2 to 12 carbon atoms, alcohol acids having 2 to 12 carbon atoms, diols having 2 to 12 carbon atoms, carboxylic acids having 2 to 12 carbon atoms, ethers having 2 to 12 carbon atoms, aldehydes having 2 to 12 carbon atoms, esters having 2 to 12 carbon atoms and glycerol, alone or mixed, is fed into the catalytic pyrolysis reactor.

In the preferred embodiment according to the invention, at least a proportion of said liquid fermentation stream comprising a stream comprising at least one oxygenated compound selected from alcohols having 2 to 6 carbon atoms, diols having 2 to 4 carbon atoms, alcohol acids having 2 to 4 carbon atoms, carboxylic acids having 2 to 6 carbon atoms, aldehydes having 2 to 12 carbon atoms and preferably 2 to 6 carbon atoms and esters having 2 to 12 carbon atoms and preferably 2 to 6 carbon atoms, alone or mixed, and very preferably, a stream comprising at least one oxygenated compound selected from ethanol, n-propanol, isopropanol, butanol, isobutanol, hexanol, acetic acid, butyric acid, hexanoic acid, lactic acid and 2,3-butylene glycol (butane-2,3-diol), alone or mixed, is recycled to the reactor in said step a) of catalytic pyrolysis.

In this case, said fermentation stream may advantageously be recycled to said step a) without an intermediate separation step. Thus, said recycled fermentation stream advantageously comprises the complete fermentation medium. In another embodiment, said fermentation stream is advantageously separated and only the separated stream comprising at least one oxygenated compound as described above is recycled to said step a).

In another preferred embodiment, said stream of oxygenated compounds is itself also separated and only at least a proportion of a stream comprising an alcohol having 2 to 12 carbon atoms is advantageously recycled to step a).

Separation of said fermentation stream advantageously allows separation of at least said stream comprising at least one oxygenated compound, water and a gaseous stream of unreacted non-condensable gases.

Separation may advantageously be performed with steam according to the techniques known by a person skilled in the art.

In particular, said separation is advantageously performed using steam derived from the catalytic pyrolysis step.

The steam may advantageously be generated by the combustion of the coke and char in the regenerator and recovered via a hot catalyst cooler or "cat-cooler", using the English-language terminology.

In this embodiment, the energy required for separation is therefore supplied by the catalytic pyrolysis step, which reinforces the synergy between the two steps of the process.

Preferably, said stream of oxygenated compounds produced by the fermentation step d), advantageously separated from the strain, comprises between 0.1 and 99.9% of water and between 99.9 and 0.1% of alcohols, diols and/or carboxylic acids and preferably between 30 and 98% of water and between 2 and 70% of alcohols, diols and/or carboxylic acids.

The fermentation step therefore makes it possible to obtain a stream of oxygenated compounds as described above, which is then at least partly recycled to the reactor of said step of catalytic pyrolysis.

Feed of this stream of oxygenated compounds into the catalytic pyrolysis step makes it possible to increase the yield of BTX in the process according to the invention.

Moreover, in the case when the stream of oxygenated compounds comes from a fermentation step according to the preferred embodiment of the invention, the process according to the invention also allows production of alcohol and preferably of ethanol from the portion of the stream of oxygenated compounds that is not recycled.

In the case when the stream of oxygenated compounds recycled to the catalytic pyrolysis step comes from a fermentation step according to the preferred embodiment of the invention, make-up of oxygenated compounds preferably selected from alcohols having 2 to 6 carbon atoms selected from ethanol, n-propanol, isopropanol, butanol, isobutanol, hexanol, diols having 2 to 4 carbon atoms selected from 2,3-butylene glycol (butane-2,3-diol), alcohol acids having 2 to 4 carbon atoms and preferably lactic acid, carboxylic acids having 2 to 6 carbon atoms selected from acetic acid, butyric acid, hexanoic acid, aldehydes having 2 to 12 carbon atoms and preferably 2 to 6 carbon atoms and esters having 2 to 12 carbon atoms and preferably 2 to 6 carbon atoms may advantageously be added in said step a) of catalytic pyrolysis.

Said make-up stream of oxygenated compounds may advantageously come from any process external to the process according to the invention allowing production of streams of oxygenated compounds, for example hydration of olefins, hydrogenation of aldehydes, hydrogenation of acids and dicarboxylic acids or hydrogenation of sugars, etherification, oxidation of alcohols, carbonylation, transesterification.

In the case when the stream of oxygenated compounds is from a fermentation step according to the preferred embodiment of the invention, hydrogen make-up may advantageously be fed into said fermentation step in the case when the composition of the feed supplied to said step does not comprise a sufficient amount of hydrogen. The use of a gaseous substrate with a low $H_2$ level leads to production of important acids. In fact, as mentioned above, supply of additional hydrogen makes it possible to improve the conversion of the CO present in the fermentation medium to alcohols (according to the balance equations of Bertsch and Müller Biotechnol Biofuels (2015) 8:210:6 CO→1 ethanol+4 $CO_2$ then $6H_2$+2 $CO_2$→1 ethanol+0.3 ATP) and promote the conversion of $CO_2$.

The make-up hydrogen may advantageously come from any process for producing hydrogen, for example a steam reforming process or a catalytic reforming process, electrolysis of water, dehydrogenation of alkanes, and its hydrogen purity is most often between 75 and 99.9 vol %.

The invention is illustrated by the following examples, which are not in any way limiting.

BRIEF DESCRIPTION OF THE FIGURES

In FIG. 1, the biomass is fed via pipe 1 into a fluidized-bed catalytic pyrolysis reactor A. A stream comprising at least one oxygenated compound is also fed via pipe 10 into the catalytic pyrolysis reactor. The gaseous effluent from catalytic pyrolysis is then sent via pipe 2 into a fractionation section B so as to recover a non-condensable gaseous effluent, comprising at least carbon monoxide (CO) and carbon dioxide ($CO_2$) via pipe 6, a liquid cut called BTX via pipe 3, a heavy liquid cut predominantly comprising compounds having a number of carbon atoms greater than 9, via pipe 4 and water via pipe 5.

Flue gases are also withdrawn from the pyrolysis reactor via pipe 9.

At least a proportion of said gaseous effluent comprising carbon monoxide (CO) and carbon dioxide ($CO_2$) is recycled via a compressor C, to the reactor of the catalytic pyrolysis step via pipe 8.

Purge of said gaseous recycle effluent is carried out via pipe 7 upstream of the compressor C.

Figure 1:
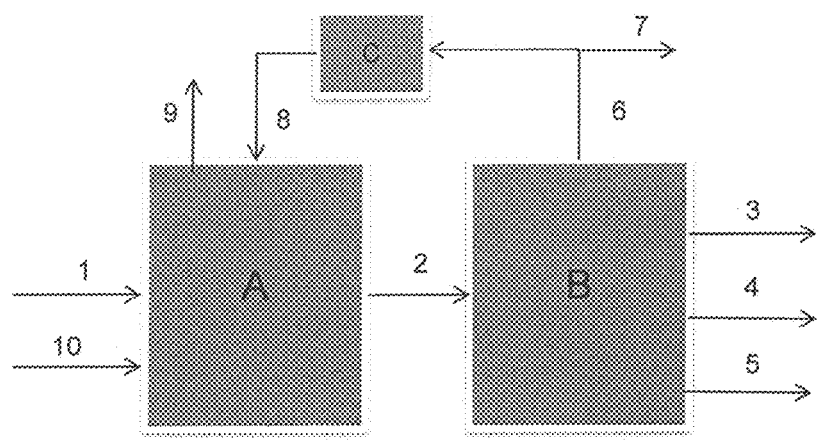
FIG. 1 illustrates the process according to the invention comprising a step of catalytic pyrolysis of biomass in which a stream of oxygenated compounds is added and FIG. 2 illustrates the preferred embodiment of the invention in which the stream of oxygenated compounds is produced in a step of fermentation of a residual effluent from the catalytic pyrolysis step of the process according to the invention.
Figure 2:
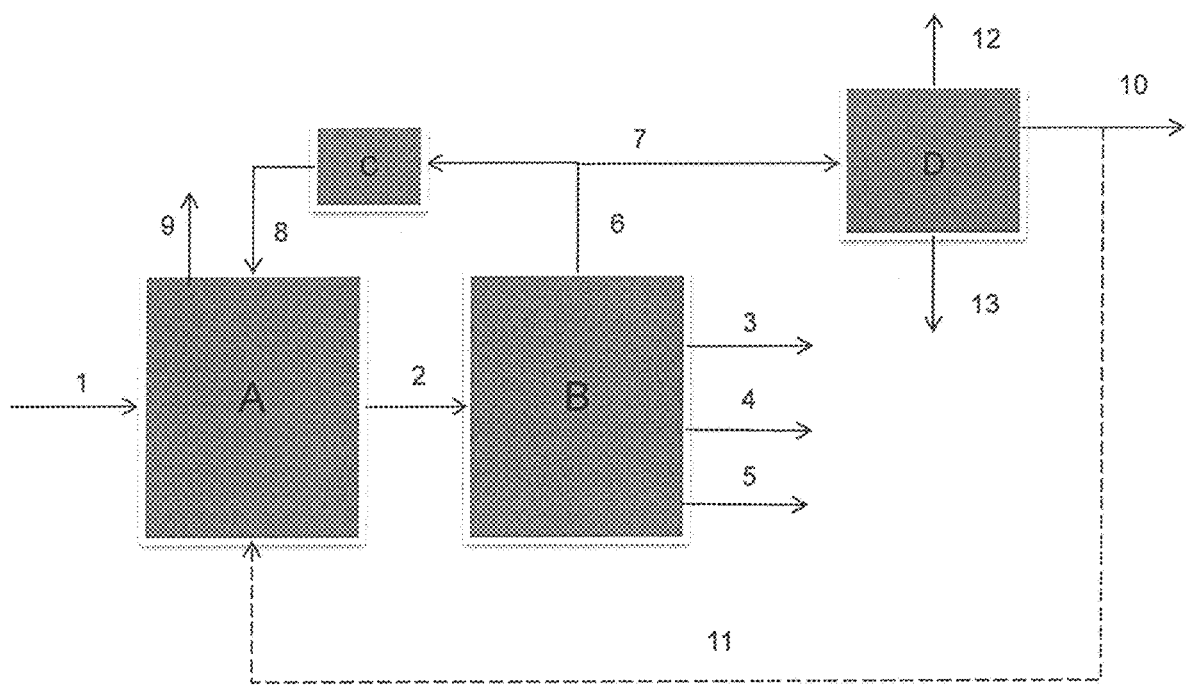

In FIG. 2, pipes 1 to 9 and the elements A, B and C are identical to those described for FIG. 1. The purge of said gaseous recycle effluent is then sent via pipe 7 to a fermentation step D that produces a liquid fermentation stream comprising at least one stream comprising at least one oxygenated compound withdrawn via pipe 10. The fermentation step D also comprises separation of the stream of fermentation liquid obtained in a stream comprising at least one oxygenated compound withdrawn via pipe 10, water withdrawn via pipe 13 and a gaseous stream of non-condensables comprising unreacted CO and $CO_2$, withdrawn via pipe 12. A portion of said liquid fermentation stream comprising at least one stream comprising at least one oxygenated compound is then recycled to the catalytic pyrolysis reactor A via pipe 11.

EXAMPLES

Example 1: Comparative: Catalytic Pyrolysis without Introduction of a Stream of Oxygenated Compounds Example 1 presents the case of catalytic pyrolysis of a variety of pine with a capacity of 2500 tonnes per day with a non-condensable portion of the gaseous effluent comprising at least CO and $CO_2$ separated from the gaseous effluent from pyrolysis being recycled to the catalytic pyrolysis reactor. The biomass is fed into the catalytic pyrolysis reactor at a rate of 104 tonnes per hour. The recycle/biomass weight ratio is 1.5 so as to be in the desired hydrodynamic conditions.

In this example the catalyst used is a commercial ZSM5 having a content of crystals of 40%. The reactor is operated at a temperature of 580° C., at a pressure of 0.2 MPa abs. and at a catalytic LHSV of 0.3 h-1.

In these conditions the yield of BTX is 15 wt % relative to the ash-free dry feed.

Example 2: According to the Invention

Example 2 corresponds to the case of catalytic pyrolysis carried out in the same operating conditions as in example 1 but for which a stream of ethanol from a process for hydrogenation of sugars is added. The case considered corresponds to an ethanol stream of 2.2 tonnes per hour.

In these conditions, the yield of BTX is improved very significantly by 4% relative to the reference case (Example 1).

Example 3: According to the Invention

Example 3 corresponds to the case of catalytic pyrolysis carried out in the same operating conditions as those in example 1 but for which the non-condensable purge of the gaseous effluent comprising at least CO and $CO_2$ is sent to a fermentation unit.

The purge in question constitutes the feed of the fermentation step and corresponds to a stream of gaseous substrate of 33 tonnes per hour having the composition presented in Table 1.

TABLE 1

| Composition of the purge constituting the feed of the fermentation unit | |
|---|---|
| Composition of the purge | wt % |
| Hydrogen | 0.5% |
| CO | 50.0% |
| $CO_2$ | 35.4% |
| Methane | 7.3% |
| Ethane | 0.5% |
| Ethylene | 6.0% |
| Propane | 0.1% |

The fermentation step is carried out using a strain of *Clostridium ljungdahlii* specifically allowing conversion of CO to ethanol in the following operating conditions:

The percentage of CO contained in the gaseous substrate that is supplied to the fermentation process is 50 wt % and the growth medium of the microorganism is the PETC medium (American Type Culture Collection (ATCC) medium 1754).

The fermentation step is supplied with the stream of gaseous substrate described above and is carried out at atmospheric pressure, with stirring at 300 rpm, at a temperature of 39° C., at a pH regulated between 5.5 and 6, and at a redox potential of 250 mV (Ag/AgCl electrode). It comprises a first phase of production of the microorganism through a chain of propagation leading to a sufficient quantity of microorganisms for inoculating the production reactors.

The production process generates a liquid fermentation stream separated from the strain extracted from the reactor, said fermentation liquid comprising 95 wt % of water, 5 wt % of ethanol and 1 wt % of residual acetic acid. The alcohols, mainly ethanol, contained in this stream are recovered by distillation leading to an azeotropic cut comprising 95% of alcohols.

Thus, a total output of 8.5 tonnes of ethanol per hour is generated. 26% of this output is recycled to the catalytic pyrolysis reactor, i.e. 2.2 tonnes per hour. The proportion of ethanol recycled to the catalytic pyrolysis reactor represents 2 wt % of the biomass fed into said catalytic pyrolysis reactor.

As in example 2, the output of BTX is improved by 4% relative to the reference case (example 1) but in addition an output of 6 wt % of ethanol relative to the ash-free dry feed is generated, which greatly improves the profitability of the process relative to example 2 and demonstrates the advantage of combining pyrolysis with a fermentation step. This combination makes it possible to upgrade the pyrolysis purge, which is generally intended to be flared into products with high added value, namely BTX and ethanol.

Example 4

Example 4 corresponds to the case of catalytic pyrolysis carried out in the same operating conditions as those in example 1 but for which the non-condensable purge of the gaseous effluent comprising at least CO and $CO_2$ is sent to a special fermentation unit for conversion of CO to ethanol and 2,3-butanediol.

The purge in question corresponds to a stream of gaseous substrate of 33 tonnes per hour having the same composition as in example 3 and presented in Table 1.

Relative to example 3, the fermentation step is carried out using a strain of *Clostridium autoethanogenum* DSMZ 10061 specifically for conversion of CO to ethanol and 2,3-butanediol in the following operating conditions:

The percentage of CO contained in the gaseous substrate that is supplied to the fermentation process is 50%, and the percentage of hydrogen is 0.5%. The growth medium is defined as follows:
Medium for growth and production of alcohols: Per litre of medium
Solution 1 ($MgCl_2.6H_2O$ 10 g/L, $CaCl_2.2H_2O$ 15 g/L): 8.33 mL
Solution 2 (NaCl 12 g/L, KCl 15 g/L): 8.33 mL
$CH_3COONH_4$ 3.00 g
Resazurine solution (1 g/L): 1.00 mL
$H_3PO_4$ (85%): 0.37 mL
Metals solution 1:1 mL
Metals solution 2:1 mL
Solution of sodium tungstate (2.94 g/L): 0.1 mL
Solution of vitamins: 10.00 mL Composition of the solutions of metals and vitamins
Metals solution 1 (per litre)
$FeSO_4.7H_2O$: 0.10 g
$ZnSO_4.7H_2O$: 0.20 g
$NiCl_2.6H_2O$: 0.02 g
HCl (38%): 30 mL
Metals solution 2 (per litre)
$MnSO_4.H_2O$: 0.5 g
$CoCl_2.6H_2O$: 0.5 g
$H_3BO_3$: 0.3 g
$NaMoO_4.2H_2O$: 0.03 g
$Na_2SeO_3$: 0.02 g
HCl (38%): 5 mL
Solution of vitamins (per litre)
Biotin: 20 mg
Folic acid: 20 mg
Pyridoxine: 10 mg
Thiamine: 50 mg
Riboflavin: 50 mg
Vitamin B3: 50 mg
Pantothenic acid: 50 mg
Vitamin B12: 50 mg
Para-aminobenzoate: 50 mg
Lipoic acid: 50 mg The fermentation step is supplied with the stream of gaseous substrate described above and is carried out at atmospheric pressure, at a temperature of 37° C., a pH regulated at 5.3 with $NH_4OH$, a redox potential maintained at 250 mV and supply of sulphur supplied by adding $Na_2S$. It comprises a first phase of production of the microorganism through a chain of propagation leading to a sufficient quantity of microorganisms for inoculating the production reactors.

The production process generates a liquid fermentation stream separated from the strain extracted from the reactor, said fermentation liquid comprising 95 wt % of water, 4.2 wt % of ethanol and 0.8 wt % of 2,3-butanediol. These alcohols are optionally recovered by distillation leading to an azeotropic cut comprising 95% of alcohols.

Thus, a total output of 6.9 tonnes of ethanol and 1.4 tonnes of 2,3-butanediol per hour is generated. 27% of this output is recycled to the catalytic pyrolysis reactor, i.e. 2.2 tonnes per hour or the same recycle flow rate as in example 3.

The proportion of ethanol and of 2,3-butanediol recycled to the catalytic pyrolysis reactor represents 2 wt % of the biomass fed into said catalytic pyrolysis reactor.

With this new operating mode of the fermentation process, production of BTX is improved by 4.5% relative to the reference case (example 1) and is therefore increased relative to example 3 (regarding the large capacity of the unit, an increase of several tenths of a point has a strong impact on the profitability of the unit) and an output of 5.8 wt % of the mixture of ethanol and 2,3-butanediol relative to the ash-free dry feed is generated, which greatly improves the profitability of the process relative to example 2. As in example 3, the combination of catalytic pyrolysis and fermentation makes it possible to upgrade the pyrolysis purge intended to be flared into products of high added value, namely BTX and alcohols with, for example 4, better selectivity for BTX relative to example 3.

The invention claimed is:
1. A process producing a BTX cut from biomass comprising at least one catalytic pyrolysis of said biomass in a fluidized-bed catalytic pyrolysis reactor in which a stream comprising at least one oxygenated compound that is alcohols having 2 to 12 carbon atoms, alcohol acids having 2 to 12 carbon atoms, diols having 2 to 12 carbon atoms, carboxylic acids having 2 to 12 carbon atoms, ethers having

2 to 12 carbon atoms, aldehydes having 2 to 12 carbon atoms, esters having 2 to 12 carbon atoms or glycerol, alone or mixed, is fed into the catalytic pyrolysis reactor.

2. The process according to claim 1, wherein the catalytic pyrolysis operates in the presence of a zeolite catalyst comprising at least one zeolite that is ZSM-5, ferrierite, zeolite Beta, zeolite Y, mordenite, ZSM-23, ZSM-57, EU-1, or ZSM-11, optionally doped with iron, gallium, zinc or lanthanum.

3. The process according to claim 1, wherein the catalytic pyrolysis produces a gaseous effluent, which is then sent to a fractionation section so as to separate at least one gaseous effluent comprising at least carbon monoxide and carbon dioxide, a liquid cut called BTX and a liquid cut comprising at least 50 wt % of compounds having a number of carbon atoms greater than 9.

4. The process according to claim 3, wherein at least a proportion of said gaseous effluent comprising carbon monoxide (CO) and carbon dioxide ($CO_2$) is recycled via a compressor to the reactor of the catalytic pyrolysis and said gaseous recycle effluent is purged, either upstream, or downstream of said compressor.

5. The process according to claim 1, wherein said stream of oxygenated compounds fed into the catalytic pyrolysis reactor comprises at least one oxygenated compound that is alcohols having 2 to 6 carbon atoms, alcohol acids having 2 to 6 carbon atoms, diols having 2 to 6 carbon atoms, carboxylic acids having 2 to 6 carbon atoms, ethers having 2 to 6 carbon atoms, aldehydes having 2 to 6 carbon atoms, esters having 2 to 6 carbon atoms or glycerol, alone or mixed.

6. The process according to claim 5, wherein the alcohols having 2 to 6 carbon atoms of said stream of oxygenated compounds are ethanol, n-propanol and isopropanol, butanol, isobutanol, 2,3-butanediol, isononanol, 2-ethylhexanol or hexanol, alone or mixed, the alcohol acids having 2 to 6 carbon atoms are lactic acid, tartaric acid, glycolic acid or citric acid, alone or mixed, the carboxylic acids having 2 to 6 carbon atoms are acetic acid, butyric acid, pyruvic acid or hexanoic acid, alone or mixed, the diols having 2 to 6 carbon atoms are ethylene glycol, diethylene glycol, triethylene glycol, propylene glycol, trimethylene glycol, butylene glycol, n-butylene glycol or 2,3-butylene glycol, alone or mixed, the ethers having 2 to 6 carbon atoms are dimethyl ether, methyl ethyl ether, diethyl ether, methyl propyl ether, methyl tert-butyl ether, ethyl tert-butyl ether, or tetrahydrofuran, alone or mixed, the aldehydes having 2 to 6 carbon atoms are ethanal, propanal, butanal, pentanal, 3-methylbutanal, hexanal, furfural or glyoxal alone or mixed, and the esters having 2 to 6 carbon atoms are methyl formate, methyl acetate, methyl propionate, methyl butanoate, methyl pentanoate, ethyl acetate, propyl acetate, isopropyl acetate, butyl acetate, isobutyl acetate, or butyl butyrate, alone or mixed.

7. The process according to claim 1, wherein said stream fed into the catalytic pyrolysis reactor is a stream comprising at least one oxygenated compound that is ethanol, butanol, isobutanol, isopropanol, n-propanol, hexanol, acetic acid, butyric acid, hexanoic acid, lactic acid or 2,3-butylene glycol (butane-2,3-diol), alone or mixed.

8. The process according to claim 7, wherein said stream comprising at least one oxygenated compound is produced in fermentation of a purge of the gaseous recycle effluent comprising CO and $CO_2$ produced by catalytic pyrolysis.

9. The process according to claim 8, wherein said stream comprising at least one oxygenated compound is separated from a fermentation stream produced by the fermentation in a separation using steam derived from the catalytic pyrolysis.

10. The process according to claim 8, wherein said fermentation step is carried out in the presence of at least one microorganism that is: *Acetogenium kivui, Acetoanaerobium noterae, Acetobacterium woodii, Alkalibaculum bacchi* CP11 (ATCC BAA-1772), *Blautia producta, Butyribacterium methylotrophicum, Coldanaerobacter subterraneus, Coldanaerobacter pacificus subterraneus, Hydrogenoformans carboxydothermus, Clostridium aceticum, Clostridium acetobutylicum, Clostridium acetobutylicum* P262 (DSM 19630 from DSMZ Germany), *Clostridium autoethanogenum* (DSM 19630 from DSMZ Germany), *Clostridium autoethanogenum* (DSM 10061 from DSMZ Germany), *Clostridium autoethanogenum* (DSM 23693 from DSMZ Germany), *Clostridium autoethanogenum* (DSM 24138 from DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ERI2 ljungdahlii* (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 from DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Sulfurreducens geobacter, Methanosarcina acetivorans, Methanosarcina barken, Morrella thermoacetica, Morrella thermoautotrophica, Oxobacter pfennigii, Peptostreptococcus productus, Ruminococcus productus, Thermoanaerobacter kivui*, and or mixtures thereof.

11. The process according to claim 10, wherein the microorganisms are *Clostridium autoethanogenum, Clostridium ljungdahlii, Clostridium aceticum, Morella thermoacetica, Acetobacterium woodiia* or *Alkalibaculum bacchi* for producing ethanol and/or acetate, *Clostridium autoethanogenum, Clostridium ljungdahlii* or *C. ragdalei* for producing 2,3-butanediol or *Clostridium carboxidivorans, Clostridium drakei, Clostridium scatologenes* or *Butyribacterium methylotrophicum* for producing butyrate and butanol, or cultures comprising a mixture of two or more of said microorganisms.

12. The process according to claim 8, wherein part of the purge of the gaseous recycle effluent comprising at least carbon monoxide and carbon dioxide, used as feed for the fermentation step in the form of gaseous substrate, has a weight ratio $H_2/CO$ of 0 to 1.2 or $H_2CO_2$ of 0 to 1.7.

13. The process according to claim 8, wherein said fermentation is carried out at a growing temperature of 20 to 80° C., at an absolute pressure of 0.1 to 0.4 MPa and at a pH of 3 to 9.

* * * * *